US008475805B2

(12) United States Patent
Fachinger et al.

(10) Patent No.: US 8,475,805 B2
(45) Date of Patent: *Jul. 2, 2013

(54) METHODS OF REDUCING CONCOMITANT INFECTIONS IN PIGS WITH A PCV2 ANTIGEN

(75) Inventors: Vicky Fachinger, Bad Soden (DE); Knut Elbers, Mittelbiberach (DE); Marion Kixmoeller, Munich (DE)

(73) Assignee: Boehringer Ingelheim Vetmedica, Inc., Saint Joseph, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/941,836

(22) Filed: Nov. 8, 2010

(65) Prior Publication Data
US 2011/0052629 A1 Mar. 3, 2011

Related U.S. Application Data

(63) Continuation of application No. 12/198,721, filed on Aug. 26, 2008, now Pat. No. 7,829,274.

(30) Foreign Application Priority Data

Sep. 4, 2007 (EP) .................................... 07115609

(51) Int. Cl.
*A61K 39/12* (2006.01)
*A61P 31/12* (2006.01)
*A61P 37/04* (2006.01)

(52) U.S. Cl.
USPC ..................................................... 424/204.1

(58) Field of Classification Search
None
See application file for complete search history.

(56) References Cited

U.S. PATENT DOCUMENTS

| | | | |
|---|---|---|---|
| 5,322,774 A | 6/1994 | Peakman et al. | |
| 5,565,205 A | 10/1996 | Petersen et al. | |
| 5,580,557 A | 12/1996 | Kramer | |
| 5,733,555 A | 3/1998 | Chu | |
| 5,885,823 A | 3/1999 | Knittel et al. | |
| 5,925,359 A | 7/1999 | Van Woensel et al. | |
| 5,968,525 A | 10/1999 | Fitzgerald et al. | |
| 6,217,883 B1 | 4/2001 | Allan et al. | |
| 6,287,856 B1 | 9/2001 | Poet et al. | |
| 6,294,176 B1 | 9/2001 | Cochran et al. | |
| 6,368,601 B1 | 4/2002 | Allan et al. | |
| 6,391,314 B1 | 5/2002 | Allan et al. | |
| 6,497,883 B1 | 12/2002 | Bublot et al. | |
| 6,517,843 B1 * | 2/2003 | Ellis et al. | 424/204.1 |
| 6,660,272 B2 | 12/2003 | Allan et al. | |
| 6,703,023 B1 | 3/2004 | Jestin et al. | |
| 6,794,163 B2 | 9/2004 | Liu et al. | |
| 6,841,364 B2 | 1/2005 | Yuan et al. | |
| 6,846,477 B2 | 1/2005 | Keich et al. | |
| 6,943,152 B1 | 9/2005 | Audonnet et al. | |
| 6,953,581 B2 | 10/2005 | Allan et al. | |
| 7,018,638 B2 | 3/2006 | Chu et al. | |
| 7,109,025 B1 * | 9/2006 | Eloit et al. | 435/320.1 |
| 7,122,192 B2 | 10/2006 | Allan et al. | |
| 7,144,698 B2 | 12/2006 | Wang et al. | |
| 7,148,015 B2 | 12/2006 | Jestin et al. | |
| 7,169,394 B2 | 1/2007 | Chu et al. | |
| 7,172,899 B2 | 2/2007 | Liu et al. | |
| 7,179,472 B2 | 2/2007 | Jestin et al. | |
| 7,192,594 B2 | 3/2007 | Haines et al. | |
| 7,211,379 B2 | 5/2007 | Ellis et al. | |
| 7,223,207 B1 | 5/2007 | Basyuk | |
| 7,223,407 B2 * | 5/2007 | Jestin et al. | 424/199.1 |
| 7,223,594 B2 | 5/2007 | Jestin et al. | |
| 7,244,433 B2 | 7/2007 | Jestin et al. | |
| 7,258,865 B2 | 8/2007 | Jestin et al. | |
| 7,261,898 B2 | 8/2007 | Jestin et al. | |
| 7,273,617 B2 | 9/2007 | Yuan et al. | |
| 7,276,353 B2 | 10/2007 | Meng et al. | |
| 7,279,166 B2 | 10/2007 | Meng et al. | |
| 7,297,537 B2 | 11/2007 | Jestin et al. | |
| 7,300,785 B2 | 11/2007 | Meerts et al. | |
| 7,312,065 B2 | 12/2007 | Roof et al. | |
| 7,314,628 B2 | 1/2008 | Jestin et al. | |
| 7,323,330 B2 | 1/2008 | Jestin et al. | |
| 7,335,361 B2 | 2/2008 | Liao et al. | |
| 7,335,362 B2 | 2/2008 | Karumanchi et al. | |
| 7,358,075 B2 | 4/2008 | Allibert et al. | |
| 7,368,117 B2 | 5/2008 | Fetzer et al. | |

(Continued)

FOREIGN PATENT DOCUMENTS

| | | |
|---|---|---|
| CA | 2305623 A1 | 4/1999 |
| CN | 1458167 A | 11/2003 |

(Continued)

OTHER PUBLICATIONS

Kim et al, The Veterinary Journal, 2003, vol. 166, pp. 251-256.*
Albina et al., "An Experimental Model for Post-weaning Multisystemic Wasting Syndrome (PMWS) in Growing Piglets". 2001, Journal of Comparative Pathology, vol. 123, pp. 292-303.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

(Continued)

*Primary Examiner* — Shanon A Foley
(74) *Attorney, Agent, or Firm* — Michael P. Morris; Wendy M. Gombert

(57) ABSTRACT

The present invention relates to a method for reducing the percentage of concomitant infections in pigs or a herd of pigs caused by pathogens other than PCV2 comprising the step administering to said pig(s) an effective amount of PCV2 antigen or an immunogenic composition comprising PCV2 antigen. It also refers to a method for improving the resistance of pigs against concomitant infections with pathogens other than PCV2, comprising the step administering to said pig(s) an effective amount of PCV2 antigen or an immunogenic composition comprising PCV2 antigen.

4 Claims, 1 Drawing Sheet

U.S. PATENT DOCUMENTS

| | | | |
|---|---|---|---|
| 7,371,395 | B2 | 5/2008 | Parisot et al. |
| 7,390,494 | B2 | 6/2008 | Jestin et al. |
| 7,405,075 | B2 | 7/2008 | Jestin et al. |
| 7,407,803 | B2 | 8/2008 | Jestin et al. |
| 7,425,444 | B2 | 9/2008 | Jestin et al. |
| 7,700,285 | B1 | 4/2010 | Eichmeyer et al. |
| 7,758,865 | B2 | 7/2010 | Jestin et al. |
| 7,829,101 | B2* | 11/2010 | Eichmeyer et al. ......... 424/204.1 |
| 7,829,273 | B2* | 11/2010 | Roof et al. ......... 435/5 |
| 7,829,274 | B2* | 11/2010 | Fachinger et al. ......... 435/5 |
| 7,833,707 | B2 | 11/2010 | Eichmeyer et al. |
| 7,838,213 | B2* | 11/2010 | Roof et al. ......... 435/5 |
| 7,838,214 | B2 | 11/2010 | Roof et al. |
| 7,910,306 | B2 | 3/2011 | Eichmeyer et al. |
| 7,914,992 | B2 | 3/2011 | Fachinger et al. |
| 7,943,298 | B2 | 5/2011 | Fachinger et al. |
| 7,951,907 | B2 | 5/2011 | Jestin et al. |
| 7,968,285 | B2 | 6/2011 | Roof et al. |
| 8,025,888 | B2 | 9/2011 | Eichmeyer et al. |
| 2003/0170270 | A1 | 9/2003 | Meng et al. |
| 2003/0215455 | A1 | 11/2003 | Reynolds et al. |
| 2004/0062775 | A1 | 4/2004 | Jestin et al. |
| 2004/0076635 | A1 | 4/2004 | Jestin et al. |
| 2004/0091502 | A1 | 5/2004 | Jestin et al. |
| 2004/0132178 | A1 | 7/2004 | Haines et al. |
| 2004/0161410 | A1 | 8/2004 | Jestin et al. |
| 2004/0253270 | A1 | 12/2004 | Meng et al. |
| 2004/0265848 | A1 | 12/2004 | Jestin et al. |
| 2005/0008651 | A1 | 1/2005 | Jestin et al. |
| 2005/0013823 | A1 | 1/2005 | Keich et al. |
| 2005/0031647 | A1 | 2/2005 | Roof et al. |
| 2005/0058653 | A1 | 3/2005 | Ellis et al. |
| 2005/0079185 | A1 | 4/2005 | Parisot et al. |
| 2005/0084497 | A1 | 4/2005 | Jestin et al. |
| 2005/0147966 | A1 | 7/2005 | Meng et al. |
| 2006/0002952 | A1 | 1/2006 | Haines et al. |
| 2006/0029617 | A1 | 2/2006 | Charreyre et al. |
| 2006/0115489 | A1 | 6/2006 | Birkett et al. |
| 2006/0204522 | A1 | 9/2006 | Kroll et al. |
| 2006/0222659 | A1 | 10/2006 | Jestin et al. |
| 2006/0233831 | A1 | 10/2006 | Parisot et al. |
| 2006/0246425 | A1 | 11/2006 | Allibert et al. |
| 2006/0286123 | A1 | 12/2006 | Fetzer et al. |
| 2007/0196879 | A1 | 8/2007 | Chabriere et al. |
| 2008/0181910 | A1 | 7/2008 | Roof et al. |
| 2008/0226669 | A1 | 9/2008 | Roof et al. |
| 2008/0233147 | A1 | 9/2008 | Jestin et al. |
| 2008/0261887 | A1 | 10/2008 | Roof et al. |
| 2008/0267995 | A1 | 10/2008 | Roof et al. |
| 2008/0279875 | A1 | 11/2008 | Roof et al. |
| 2008/0279876 | A1 | 11/2008 | Roof et al. |
| 2008/0279889 | A1 | 11/2008 | Roof et al. |
| 2009/0016992 | A1 | 1/2009 | Eichmeyer et al. |
| 2009/0022751 | A1 | 1/2009 | Eichmeyer et al. |
| 2009/0042095 | A1 | 2/2009 | Eichmeyer et al. |
| 2010/0184016 | A1 | 7/2010 | Lefebvre et al. |
| 2010/0189743 | A1* | 7/2010 | Jestin et al. ......... 424/204.1 |
| 2011/0033495 | A1 | 2/2011 | Roof et al. |
| 2011/0091499 | A1 | 4/2011 | Fachinger et al. |
| 2011/0217327 | A1 | 9/2011 | Roof et al. |
| 2011/0274710 | A1 | 11/2011 | Eichmeyer et al. |

FOREIGN PATENT DOCUMENTS

| | | |
|---|---|---|
| EP | 1281760 A1 | 2/2003 |
| EP | 1386617 A1 | 2/2004 |
| WO | 8906972 A1 | 8/1989 |
| WO | 9007935 A1 | 7/1990 |
| WO | 9118627 A1 | 12/1991 |
| WO | 9203157 A1 | 3/1992 |
| WO | 9316726 A2 | 9/1993 |
| WO | 9530437 A1 | 11/1995 |
| WO | 9918214 A1 | 4/1999 |
| WO | 9929717 A3 | 6/1999 |
| WO | 9929871 A3 | 6/1999 |
| WO | 0047756 A1 | 8/2000 |
| WO | 0077188 A2 | 12/2000 |
| WO | 0116330 A2 | 3/2001 |
| WO | 0117550 A2 | 3/2001 |
| WO | 0117551 A2 | 3/2001 |
| WO | 0117556 A1 | 3/2001 |
| WO | 0249666 A2 | 6/2002 |
| WO | 03003941 A2 | 1/2003 |
| WO | 2004058142 A2 | 7/2004 |
| WO | 2004069184 A2 | 8/2004 |
| WO | 2005009462 A2 | 2/2005 |
| WO | 2005112995 A1 | 12/2005 |
| WO | 2006072065 A2 | 7/2006 |
| WO | 2006113372 A2 | 10/2006 |
| WO | 2006113373 A2 | 10/2006 |
| WO | 2007028823 A1 | 3/2007 |
| WO | 2007076520 A2 | 7/2007 |
| WO | 2009030684 A2 | 3/2009 |
| WO | 2009103037 A1 | 8/2009 |

OTHER PUBLICATIONS

Allan et al., "Guest Editorial, PCV-2 infection in swine; more than just postweaning multisystemic wasting syndrome". 2003, The Veterinary Journal, vol. 166, pp. 222-223.

Allan et al., "Letters, Immunostimulations, PCV-2 and PMWS". Aug. 2000, The Veterinary Record, pp. 170-171.

Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.

Allan et al., "PMWS/PCVD: Diagnosis, Disease, and Control: What do we know?" 2006, Proceedings of the 19th IPVS Congress, Copenhagen, Denmark, vol. 1, pp. 1-9.

Allan et al., "Porcine circoviruses: a review". 2000, Journal of Veterinary Diagnostic Investigation, vol. 12, pp. 3-14.

Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.

Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.

Blanchard et al., "Protection of swine against post-weaning multisystemic wasting syndrome (PMWS) by porcine circovirus type 2 (PCV2) proteins". 2003, Vaccine, vol. 21, pp. 4565-4575.

Boisseson et al., "Molecular characterization of Porcine circovirus type 2 isolates from post-weaning multisystemic wasting syndrome-affected and non-affected pigs". 2004, Journal of General Virology, vol. 85, pp. 293-304.

Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.

Chae, C., "Postweaning multisystemic wasting syndrome: a review of aetiology, diagnosis and pathology". 2004, The Veterinary Journal, vol. 168, pp. 41-49.

Charbonneau, G., "Canadian Experiences with Porcine Circovirus Associated Disease". 2007, Iowa Pork Congress.

Cheung et al., "Kinetics of porcine circovirus type 2 replication". 2002, Archives of Virology, vol. 147, p. 43-58.

Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.

Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.

Fachinger et al., "The effect of vaccination against porcine circovirus type 2 in pigs suffering from porcine respiratory disease complex". 2008, Vaccine, vol. 26, pp. 1488-1499.

Fan et al., "Immunogenicity of Empty Capsids of Porcine Circovirus Type 2 Produced in Insect Cells". 2007, Veterinary Research Communications, vol. 31, pp. 487-496.

Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Immunity against PCV2 Infection in Pigs". Jun. 2004, Journal of Virology, vol. 78, No. 12, pp. 6297-6303.

Genbank Accession No. AAC61738, Version AAC61738.1 GI:3661517, Sep. 29, 1998.

Groner, et al., The Biology of Baculoviruses, vol. 1, Biological Properties and Molecular Biology, 1986, Chapter 9, Specificity and Safety of Baculoviruses, pp. 177-202.

International Search Report for PCT/EP2008/061566 mailed on Jun. 18, 2009.

Inumaru et al., "Expression of biologically active recombinant porcinee GM-CSF by baculovirus gene expression system". 1998, Immunology and Cell Biology, vol. 76, pp. 195-201.

Ju et al., "Immunogenicity of a recombinant pseudorabies virus expressing ORF1-ORF2 fusion protein of porcine circovirus type 2". 2005, Veterinary Microbiology, vol. 109, pp. 179-190.

Kamstrup, et al., "Immunisation against PCV2 structural protein by DNA vaccination of mice". 2004, Vaccine, vol. 22, pp. 1358-1361.

Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.

Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.

Kim et al., "Enteritis associated with procine circovirus 2 in pigs". 2004, The Canadian Journal of Veterinary Research, vol. 68, pp. 218-221.

Kixmoller et al., "Reduction of PMWS-associated clinical signs and co-infections by vaccination against PCV2". 2008, Vaccine, vol. 26, pp. 3443-3451.

Kost, et al., "Recombinant baculoviruses as mammalian cell gene-delivery vectors". Apr. 2002, Trends in Biotechnology, vol. 20, No. 4, pp. 173-180.

Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.

Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.

Liu et al., "Bacterial Expression of an Immunologically Reactive PCV2 ORF2 Fusion Protein". 2001, Protein Expression and Purification, vol. 21, pp. 115-120.

Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.

Mackinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.

Mahe et al., "Differential recognition of ORF2 protein from type 1 and type 2 porcine circoviruses and identification of immunorelevant epitopes". 2000, Journal of General virology, vol. 81, pp. 1815-1824.

Maranga et al., "Virus-Like Particle Production at Low Multiplicities of Infection With the Baculovirus Insect Cell System". Aug. 2003, Biotechnology and Bioengineering, vol. 84, No. 2, pp. 246-253.

McNeilly et al., Evaluation of a porcine circovirus type 2-specific antigen-captive enzyme-linked immunosorbent assay for the diagnosis of postweaning multisystemic wasting sydrome in pigs: comparison with virus isolation, immunohistochemistry, and the polymerase chain reaction, 2002, Journal of Veterinary Diagnostic Investigation, vol. 14, pp. 106-112.

Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.

Morales et al., "Serendipitous Discovery and X-Ray Structure of a Human Phosphate Binding Apolipoprotein". Mar. 2006, Structure, vol. 14, pp. 601-609.

Morris et al., "Characterization of Procuctive and Non-productive ACMNPV Infection in Selected Insect Cell LInes". 1993, Virology, vol. 197, pp. 339-348.

Morris et al., "Promoter Influence on Baculovirus-Mediated Gene Expression in Permissive and Nonpermissive Insect Cell Lines". Dec. 1992, Journal of Virology, vol. 66, No. 12, pp. 7397-7405.

Nawagitgul et al., "Modified Indirect prcine Circovirus (PCV) Type 2-Based and Recombinant Capsid Protein (ORF-2)-Based Enzyme-Linked Immunosorbent Assays for Detection of Antibodies to PCV, Clinical and Diagnostic Laboratory Immunology". Jan. 2002, vol. 9, No. 1 pp. 33-40.

Nawagitgul et al., "Open reading frame 2 of porcine circovirus type 2 encodes a major capsid protein". 2000, Journal of General Virology, vol. 81, pp. 2281-2287.

Okuda et al., "Experimental reproduction of post-weaning multisystemic wasting syndrome in cesarean-derived, colostrum-deprived piglets inoculated with porcine circovirus type 2 (PCV2): investigation of quantitative PCV2 distribution and antibody responses". 2003, Journal of Veterinary Diagnostic Investigation, vol. 15, pp. 107-114.

Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.

Opriessnig et al., "Porcine Circovirus Type Infection Decreases the Efficacy of a Modified Live Porcine Reproductive and Respiratory Syndrome Virus Vaccine". Aug. 2006, Clinical and Vaccine Immunology, vol. 13, No. 8, pp. 923-929.

Ponsich, A., "Etude Preliminaire De L'Impact Du Circovac Sur L'infection Par Le PCV2 En Maternite". Nov. 1981.

Quintana et al., "Clinical and pathological observations on pigs with postweaning multisystemic wasting syndrome". 2001, The Veterinary Record, vol. 149, pp. 357-361.

Rovira et al., "Experimental Inoculation of Conventional Pigs with Porcine Reproductive an Respiratory Syndrome Virus and Porcine Circovirus 2". Apr. 2002, Journal of Virology, vol. 76, No. 7, pp. 3232-3239.

Rueda et al., "Effect of different baculovirus inactivation procedures on the integrity and immuogenicity of porcine parvovirus-like particles". 2001, Vaccine, vol. 19, pp. 726-734.

Segales et al., "Changes in peripheral blood leukocyte populations in pigs with natural postweaning multisystemic wasting syndrome (PMWS)". 2001, Veterinary Immunology and Immunopathology, vol. 81, pp. 37-44.

Segales et al., "Epidemiology of porcine circovirus type 2 infection: what do we know?" 2003, Pig News and Information, vol. 24, No. 4, pp. 103N-110N.

Segales et al., "Postweaning multisystemic wasting syndrom (PMWS) in pigs. A review". 2002, Veterinary Quarterly, vol. 24, No. 3, pp. 109-124.

Segales, J. "Postweaning multisystemic wasting syndrome (PMWS) in pigs: paradigm of a multifactorial disease". Oct. 2005, Presentation at Genetics and Genomics for Animal Health, Wellcome Trust Genome Campus, Hinxton, UK.

Sibila et al., "Use of a polymerase chain reaction assay and an ELISA to monitor procine circovirus type 2 infection in pigs from farms with and without postweaning multisystemic wasting syndrome". Jan. 2004, American Journal of Veterinary Research, vol. 65, No. 1, pp. 88-92.

Sorden et al., "Development of a polyclonal-antibody-based immunohistochemical method for the detection of type 2 porcine circovirus in formalin-fixed, paraffin-embedded tissue." 1999, Journal of Veterinary Diagnostic Investigation, vol. 11, pp. 528-530.

Vansickle, J., "Circovirus Grips Industry". Jul. 15, 2006, National Hog Farmer.

Vasconcelos et al., "Swine and Poultry Pathogens: the Complete Genome Sequences of Two Strains of Mycoplasma hyopneumoniae and a Strain of Mycoplasma synoviae". Aug. 2005, Journal of Bacteriology, vol. 187, No. 16, pp. 5568-5577.

Vido Swine Technical Group-Linking Knowledge to practical solutions "Vaccination Guidelines for Swine". Jun. 2004, www.vido.org.

Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.

Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.

Web site: "Does stress-free livestock mean safer food?" http://www.foodnavigator.com/Financial-Industry/Does-stress-free-livestock-mean-safer-food Accessed on: Jun. 4, 2004.

Written Opinion of the International Searching Authority for PCT/EP2008/061566 mailed on Jun. 18, 2009.

Abstract in English of CN1458167, dated Nov. 26, 2003.

Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb 2008, Technical Bulletin, www.bivetmedica.com/swine-research/MycoFLEX-Mycoplasma-immunity_TB2.pdf.

Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletin, www.bivetmedica.com/swine-research/MycoFLEX-Mycoplasma-immunity_TB2.pdf; 14 pages.

Boehringer Ingelheim Vetmedica, Inc., Ingelvacâ Circoflexä Material Safety Data Sheet, Online Oct. 2006, pp1-10, URL:http://bi-vetmedica.com/sites/default/files/ingelvac-circoflex-msds.pdf.

Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.

Chae, C. "A review of porcine circovirus 2-associated syndromes and diseases". The Veterinary Journal, vol. 169, No. 3, 2005, pp. 326-336.

Chen et al., "Serological survey of serum antibodies against porcine circovirus type 2 (PCV2) in swine, chicken, duck, goat and cattle fromZhejiang province, China". Revue de Médecine Vétérinaire, vol. 158, Nos. 8-9, 2007, pp. 458-462.

Ellis et al., "Lack of antibodies to porcine circovirus type 2 virus in beef and dairy cattle and horses in western Canada". Canadian Veterinary Journal, vol. 42, 2001, pp. 461-464.

Ellis et al., "Porcine circovirus-2 and concurrent infections in the field". Veterinary Microbiology, vol. 98, No. 2, Feb. 2004, pp. 159-163.

Gagrcin et al., "Complex of Swine Respiratory Diseases-Strategy of control in light of latest knowledge". Veterinarski Glasnik, vol. 58, No. 7-8, 2004, pp. 409-418.

Genbank Accession# AAF87231, PCV2 ORF2 Protein, 2000.

Ha et al., "Outbreak of salmonellosis in pigs with postweaning multisystemic wasting syndrome". Veterinary Record, vol. 156, No. 18, Apr. 2005, pp. 583-584.

Jensen et al., "Distinction between Porcine Circovirus Type 2 Enteritis and Porcine Proliferative Enteropathy caused by Lawsonia intracellularis". Journal of Comparative Pathology, vol. 135, 2006, pp. 176-182.

Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.

Opriessnig et al., "Derivation of porcine circovirus type 2-negative pigs from positive breeding herds". Journal of Swine Health and Production, vol. 12, No. 4, Jul. and Aug. 2004, pp. 186-191.

Opriessnig et al., "Experimental Reproduction of Postweaning Multisystemic Wasting Syndrome in Pigs by Dual Infection with Mycoplasma hyopneumoniae and Porcine Circovirus Type 2". Veterinary Pathology, vol. 41, No. 6, Nov. 2004, pp. 624-640.

Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.

Segales et al., "Granulomatous Enteritis and Lymphadenitis in Iberian Pigs Naturally Infected with Lawsonia intracellularis". Veterinary Pathology, vol. 38, No. 3, 2001, pp. 343-346.

Sequence alignment of SEQ ID No. 11 with UniProt database accession No. 091862 of Meehan et al., entered Nov. 1, 1998.

Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.

Kim et al., "Efficacy of different disinfectants in vitro against porcine circovirus type 2". The Veterinary Record, vol. 164, May 2009, pp. 599-600.

Riggs et al., "Protective Monoclonal Antibody Defines a Circumsporozoite-Like Glycoprotein Exoantigen of Cryptosporidium parvum Sporozoites and Merozoites". The Journal of Immunology, vol. 158, 1997, pp. 1787-1795.

Royer et al., "Susceptibility of porcine circovirus type 2 to commercial and laboratory disinfectants". Journal of Swine Health and Production, vol. 9, No. 6, 2001, pp. 281-284.

* cited by examiner

FIG. 1A:
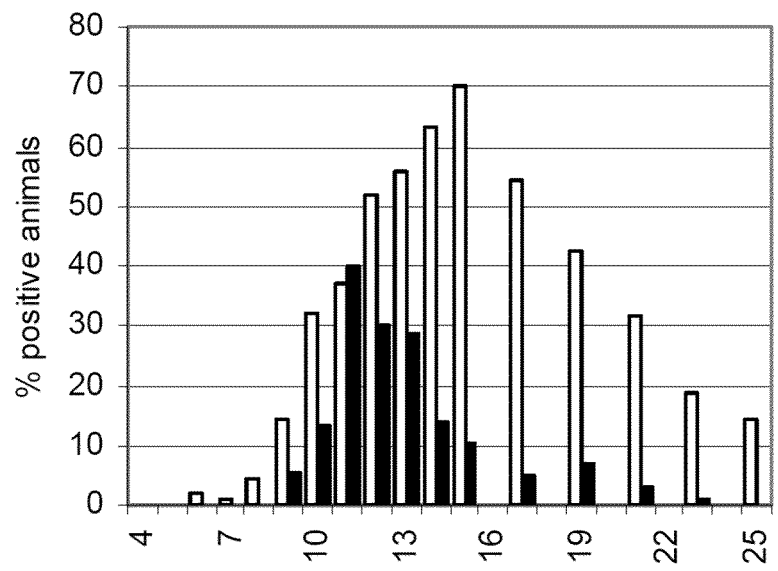
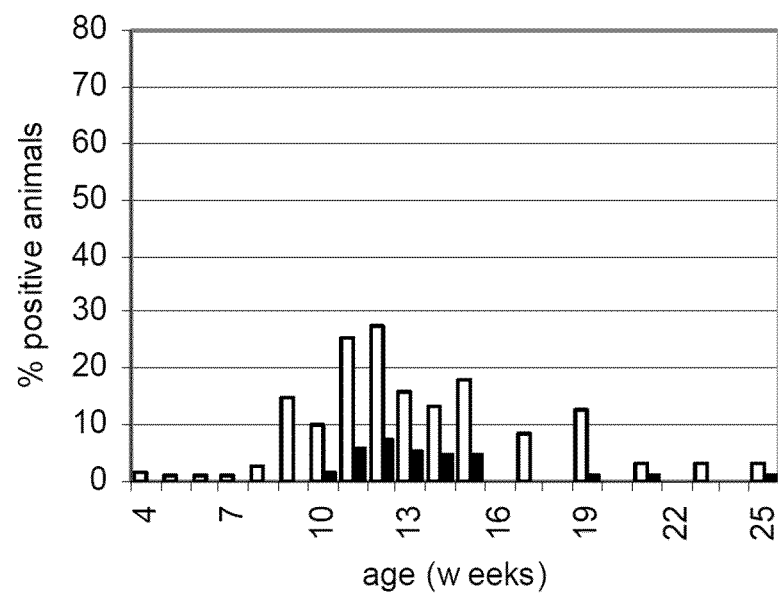
FIG. 1B:

SEQUENCE LISTING

<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence.

<400> SEQUENCE: 1 ccgccatg                                                                    8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence.

<400> SEQUENCE: 2 gaattc                                                                      6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc      60
ttggccagat cctccgccgc cgcccctggc tcgtccaccc ccgccaccgc taccgttgga     120
gaaggaaaaa tggcatcttc aacacccgcc tctcccgcac cttcggatat actgtggaga     180
aggaaaaatg gcatcttcaa cacccgcctc tcccgcacct tcggatatac tgtgacgact     240
ttgttccccc gggaggggggg accaacaaaa tctctatacc ctttgaatac tacagaataa     300
gaaaggttaa ggttgaattc tggccctgct ccccatcac ccagggtgat aggggagtgg      360
gctccactgc tgttattcta gatgataact ttgtaacaaa ggccacagcc ctaacctatg     420
acccatatgt aaactactcc tcccgccata caatccccca acccttctcc taccactccc     480
gttacttcac acccaaacct gttcttgact ccactattga ttacttccaa ccaaataaca     540
aaaggaatca gctttggctg aggctacaaa cctctagaaa tgtggaccac gtaggcctcg     600
gcactgcgtt cgaaaacagt aaatacgacc aggactacaa tatccgtgta accatgtatg     660
tacaattcag agaatttaat cttaaagacc ccccacttaa accctaaatg aat             713

<210> SEQ ID NO 4
<211> LENGTH: 713

```
<212> TYPE: DNA
<213> ORGANISM: Porcine circovirus

<400> SEQUENCE: 4
ccgccatgac gtatccaagg aggcgttacc gcagaagaag acaccgcccc cgcagccatc    60
ttggccagat cctccgccgc cgcccctggc tcgtccaccc ccgccaccgc taccgttgga   120
gaaggaaaaa tggcatcttc aacacccgcc tctcccgcac cttcggatat actgtcaagg   180
ctaccacagt cacaacgccc tcctgggcgg tggacatgat gagatttaat attgacgact   240
tgttccccc gggaggggg accaacaaaa tctctatacc ctttgaatac tacagaataa   300
gaaaggttaa ggttgaattc tggccctgct cccccatcac ccagggtgat aggggagtgg   360
gctccactgc tgttattcta gatgataact ttgtaacaaa ggccacagcc ctaacctatg   420
acccatatgt aaactactcc tcccgccata caatccccca accttctcc taccactccc   480
gttacttcac acccaaacct gttcttgact ccactattga ttacttccaa ccaaataaca   540
aaaggaatca gctttggctg aggctacaaa cctctagaaa tgtggaccac gtaggcctcg   600
gcactgcgtt cgaaaacagt aaatacgacc aggactacaa tatccgtgta accatgtatg   660
tacaattcag agaatttaat cttaaagacc ccccacttga accctaagaa ttc           713

<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg His Arg Pro Arg
1               5                  10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220
```

```
Asn Leu Lys Asp Pro Pro Leu Lys Pro
225                 230

<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
                35                  40                  45

Leu Ser Arg Thr Phe Gly Tyr Thr Val Lys Ala Thr Thr Val Thr Thr
        50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
        130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7
gcggccgcgg gaattcgatc cgccatgacg tatccaagga ggcgttaccg cagaagaaga      60
caccgccccc gcagccatct tggccagatc ctccgccgcc gcccctggct cgtccacccc     120
cgccaccgct accgttggag aaggaaaaat ggcatcttca acacccgcct ctcccgcacc     180
ttcggatata ctgtcaaggc taccacagtc acaacgccct cctgggcggt ggacatgatg     240
agatttaata ttgacgactt tgttcccccg ggagggggga ccaacaaaat ctctataccc     300
tttgaatact acagaataag aaaggttaag gttgaattct ggccctgctc ccccatcacc     360
```

-continued

| | |
|---|---|
| cagggtgata ggggagtggg ctccactgct gttattctag atgataactt tgtaacaaag | 420 |
| gccacagccc taacctatga cccatatgta aactactcct cccgccatac aatcccccaa | 480 |
| cccttctcct accactcccg ttacttcaca cccaaacctg ttcttgactc cactattgat | 540 |
| tacttccaac caaataacaa aaggaatcag ctttggctga ggctacaaac ctctagaaat | 600 |
| gtggaccacg taggcctcgg cactgcgttc gaaaacagta aatacgacca ggactacaat | 660 |
| atccgtgtaa ccatgtatgt acaattcaga gaatttaatc ttaaagaccc cccacttgaa | 720 |
| ccctaagaat tctatcacta gtgaattcgc ggccgc | 756 |

<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF-2
    construct, which includes baculovirus and pGEM T-easy coding
    sequences.

<400> SEQUENCE: 8

| | |
|---|---|
| aagctttact cgtaaagcga gttgaaggat catatttagt tgcgtttatg agataagatt | 60 |
| gaaagcacgt gtaaaatgtt tcccgcgcgt tggcacaact atttacaatg cggccaagtt | 120 |
| ataaaagatt ctaatctgat atgttttaaa acacctttgc ggcccgagtt gtttgcgtac | 180 |
| gtgactagcg aagaagatgt gtggaccgca gaacagatag taaaacaaaa ccctagtatt | 240 |
| ggagcaataa tcgatttaac caacacgtct aaatattatg atggtgtgca ttttttgcgg | 300 |
| gcgggcctgt tatacaaaaa aattcaagta cctggccaga ctttgccgcc tgaaagcata | 360 |
| gttcaagaat ttattgacac ggtaaaagaa tttacagaaa agtgtcccgg catgttggtg | 420 |
| ggcgtgcact gcacacacgg tattaatcgc accggttaca tggtgtgcag atatttaatg | 480 |
| cacaccctgg gtattgcgcc gcaggaagcc atagatagat cgaaaaagc cagaggtcac | 540 |
| aaaattgaaa gacaaaatta cgttcaagat ttattaattt aattaatatt atttgcattc | 600 |
| tttaacaaat actttatcct atttttcaaat tgttgcgctt cttccagcga accaaaacta | 660 |
| tgcttcgctt gctccgttta gcttgtagcc gatcagtggc gttgttccaa tcgacggtag | 720 |
| gattaggccg gatattctcc accacaatgt tggcaacgtt gatgttacgt ttatgctttt | 780 |
| ggttttccac gtacgtcttt tggccggtaa tagccgtaaa cgtagtgccg tcgcgcgtca | 840 |
| cgcacaacac cggatgtttg cgcttgtccg cggggtattg aaccgcgcga tccgacaaat | 900 |
| ccaccacttt ggcaactaaa tcggtgacct gcgcgtcttt tttctgcatt atttcgtctt | 960 |
| tcttttgcat ggtttcctgg aagccggtgt acatgcggtt tagatcagtc atgacgcgcg | 1020 |
| tgacctgcaa atctttggcc tcgatctgct tgtccttgat ggcaacgatg cgttcaataa | 1080 |
| actcttgttt tttaacaagt tcctcggttt tttgcgccac caccgcttgc agcgcgtttg | 1140 |
| tgtgctcggt gaatgtcgca atcagcttag tcaccaactg tttgctctcc tcctcccgtt | 1200 |
| gtttgatcgc gggatcgtac ttgccggtgc agagcacttg aggaattact tcttctaaaa | 1260 |
| gccattcttg taattctatg gcgtaaggca atttggactt cataatcagc tgaatcacgc | 1320 |
| cggatttagt aatgagcact gtatgcggct gcaaatacag cgggtcgccc ttttcacga | 1380 |
| cgctgttaga ggtagggccc ccattttgga tggtctgctc aaataacgat tgtatttat | 1440 |
| tgtctacatg aacacgtata gctttatcac aaactgtata ttttaaactg ttagcgacgt | 1500 |
| ccttggccac gaaccggacc tgttggtcgc gctctagcac gtaccgcagg ttgaacgtat | 1560 |
| cttctccaaa tttaaattct ccaattttaa cgcgagccat tttgatacac gtgtgtcgat | 1620 |

```
tttgcaacaa ctattgtttt ttaacgcaaa ctaaacttat tgtggtaagc aataattaaa    1680
tatgggggaa catgcgccgc tacaacactc gtcgttatga acgcagacgg cgccggtctc    1740
ggcgcaagcg gctaaaacgt gttgcgcgtt caacgcggca acatcgcaa aagccaatag    1800
tacagttttg atttgcatat taacggcgat tttttaaatt atcttattta ataaatagtt    1860
atgacgccta caactccccg cccgcgttga ctcgctgcac ctcgagcagt tcgttgacgc    1920
cttcctccgt gtggccgaac acgtcgagcg ggtggtcgat gaccagcggc gtgccgcacg    1980
cgacgcacaa gtatctgtac accgaatgat cgtcgggcga aggcacgtcg gcctccaagt    2040
ggcaatattg gcaaattcga aaatatatac agttgggttg tttgcgcata tctatcgtgg    2100
cgttgggcat gtacgtccga acgttgattt gcatgcaagc cgaaattaaa tcattgcgat    2160
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca    2520
tgaccccccgt agtgacaacg atcacgccca aaagaactgc cgactacaaa attaccgagt    2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aatttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aaatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aatttatttt tcacataaac    3480
tagacgcctt gtcgtcttct tcttcgtatt ccttctcttt ttcattttc tcctcataaa    3540
aattaacata gttattatcg tatccatata tgtatctatc gtatagagta aattttttgt    3600
tgtcataaat atatatgtct tttttaatgg ggtgtatagt accgctgcgc atagttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
```

```
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc ctctcccgca    4320
ccttcggata tactgtcaag gctaccacag tcacaacgcc ctcctgggcg gtggacatga    4380
tgagatttaa tattgacgac tttgttcccc cgggaggggg gaccaacaaa atctctatac    4440
cctttgaata ctacagaata agaaaggtta aggttgaatt ctggccctgc tcccccatca    4500
cccagggtga taggggagtg ggctccactg ctgttattct agatgataac tttgtaacaa    4560
aggccacagc cctaacctat gacccatatg taaactactc ctcccgccat acaatccccc    4620
aacccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg gccgctccag aattctagaa    4920
ggtacccggg atccttttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga aacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580
aataattcat taaatttata atcttttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactcgacg taaacacgtt aaataaagct    5940
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttttgg aattatttct    6120
gattgcgggc gtttttgggc gggtttcaat ctaactgtgc ccgattttaa ttcagacaac    6180
acgttagaaa gcgatggtgc aggcggtggt aacatttcag acggcaaatc tactaatggc    6240
ggcggtggtg gagctgatga taaatctacc atcggtggag gcgcaggcgg ggctggcggc    6300
ggaggcggag gcgaggtgg tggcggtgat gcagacggcg gtttaggctc aaatgtctct    6360
ttaggcaaca cagtcggcac ctcaactatt gtactggttt cgggcgccgt ttttggtttg    6420
```

```
accggtctga gacgagtgcg attttttttcg tttctaatag cttccaacaa ttgttgtctg    6480
tcgtctaaag gtgcagcggg ttgaggttcc gtcggcattg gtggagcggg cggcaattca    6540
gacatcgatg gtggtggtgg tggtggaggc gctggaatgt taggcacggg agaaggtggt    6600
ggcggcggtg ccgccggtat aatttgttct ggtttagttt gttcgcgcac gattgtgggc    6660
accggcgcag gcgccgctgg ctgcacaacg gaaggtcgtc tgcttcgagg cagcgcttgg    6720
ggtggtggca attcaatatt ataattggaa tacaaatcgt aaaaatctgc tataagcatt    6780
gtaatttcgc tatcgtttac cgtgccgata tttaacaacc gctcaatgta agcaattgta    6840
ttgtaaagag attgtctcaa gctcgccgca cgccgataac aagccttttc attttttacta   6900 cagcattgta gtggcgagac acttcgctgt cgtcgacgta catgtatgct tgttgtcaa    6960 aaacgtcgtt ggcaagcttt aaaatattta aagaacatc tctgttcagc accactgtgt    7020
tgtcgtaaat gttgtttttg ataatttgcg cttccgcagt atcgacacgt tcaaaaaatt    7080
gatgcgcatc aattttgttg ttcctattat tgaataaata agattgtaca gattcatatc    7140
tacgattcgt catggccacc acaaatgcta cgctgcaaac gctggtacaa ttttacgaaa    7200
actgcaaaaa cgtcaaaact cggtataaaa taatcaacgg gcgctttggc aaaatatcta    7260
ttttatcgca caagcccact agcaaattgt atttgcagaa acaatttcg gcgcacaatt    7320 ttaacgctga cgaaataaaa gttcaccagt taatgagcga ccacccaaat tttataaaaa    7380
tctattttaa tcacggttcc atcaacaacc aagtgatcgt gatggactac attgactgtc    7440
ccgatttatt tgaaacacta caaattaaag gcgagctttc gtaccaactt gttagcaata    7500
ttattagaca gctgtgtgaa gcgctcaacg atttgcacaa gcacaatttc atacacaacg    7560
acataaaact cgaaaatgtc ttatatttcg aagcacttga tcgcgtgtat gtttgcgatt    7620
acggattgtg caaacacgaa aactcactta gcgtgcacga cggcacgttg gagtatttta    7680
gtccggaaaa aattcgacac acaactatgc acgtttcgtt tgactggtac gcggcgtgtt    7740
aacatacaag ttgctaacgt aatcatggtc atagctgttt cctgtgtgaa attgttatcc    7800
gctcacaatt ccacacaaca tacgagccgg aagcataaag tgtaaagcct ggggtgccta    7860
atgagtgagc taactcacat taattgcgtt gcgctcactg cccgctttcc agtcgggaaa    7920
cctgtcgtgc cagctgcatt aatgaatcgg ccaacgcgcg gggagaggcg gtttgcgtat    7980
tgggcgctct tccgcttcct cgctcactga ctcgctgcgc tcggtcgttc ggctgcggcg    8040
agcggtatca gctcactcaa aggcggtaat acggttatcc acagaatcag gggataacgc    8100
aggaaagaac atgtgagcaa aaggccagca aaaggccagg aaccgtaaaa aggccgcgtt    8160
gctggcgttt ttccataggc tccgcccccc tgacgagcat cacaaaaatc gacgctcaag    8220
tcagaggtgg cgaaacccga caggactata aagataccag gcgtttcccc ctggaagctc    8280
cctcgtgcgc tctcctgttc cgaccctgcc gcttaccgga tacctgtccg cctttctccc    8340
ttcgggaagc gtggcgcttt ctcatagctc acgctgtagg tatctcagtt cggtgtaggt    8400
cgttcgctcc aagctgggct gtgtgcacga accccccgtt cagcccgacc gctgcgcctt    8460
atccggtaac tatcgtcttg agtccaaccc ggtaagacac gacttatcgc cactggcagc    8520
agccactggt aacaggatta gcagagcgag gtatgtaggc ggtgctacag agttcttgaa    8580
gtggtggcct aactacggct acactagaag gacagtattt ggtatctgcg ctctgctgaa    8640
gccagttacc ttcggaaaaa gagttggtag ctcttgatcc ggcaaacaaa ccaccgctgg    8700
tagcggtggt ttttttgttt gcaagcagca gattacgcgc agaaaaaaag gatctcaaga    8760
agatcctttg atcttttcta cggggtctga cgctcagtgg aacgaaaact cacgttaagg    8820
```

-continued

```
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga gacccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
agcactgcat aattctctta ctgtcatgcc atccgtaaga tgcttttctg tgactggtga   9480
gtactcaacc aagtcattct gagaatagtg tatgcggcga ccgagttgct cttgcccggc   9540
gtcaatacgg gataataccg cgccacatag cagaacttta aaagtgctca tcattggaaa   9600
acgttcttcg gggcgaaaac tctcaaggat cttaccgctg ttgagatcca gttcgatgta   9660
acccactcgt gcacccaact gatcttcagc atcttttact ttcaccagcg tttctgggtg   9720
agcaaaaaca ggaaggcaaa atgccgcaaa aaagggaata agggcgacac ggaaatgttg   9780
aatactcata ctcttccttt ttcaatatta ttgaagcatt tatcagggtt attgtctcat   9840
gagcggatac atatttgaat gtatttagaa aaataaacaa ataggggttc cgcgcacatt   9900
tccccgaaaa gtgccacctg acgtctaaga aaccattatt atcatgacat taacctataa   9960
aaataggcgt atcacgaggc cctttcgtct cgcgcgtttc ggtgatgacg gtgaaaacct  10020
ctgacacatg cagctcccgg agacggtcac agcttgtctg taagcggatg ccgggagcag  10080
acaagcccgt cagggcgcgt cagcgggtgt tggcgggtgt cggggctggc ttaactatgc  10140
ggcatcagag cagattgtac tgagagtgca ccatatgcgg tgtgaaatac cgcacagatg  10200
cgtaaggaga aaataccgca tcaggcgcca ttcgccattc aggctgcgca actgttggga  10260
agggcgatcg gtgcgggcct cttcgctatt acgccagctg gcgaaagggg gatgtgctgc  10320
aaggcgatta agttgggtaa cgccagggtt ttcccagtca cgacgttgta aaacgacggc  10380
cagtgcc                                                             10387

<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg Arg His His Pro Pro Ser
1               5                   10                  15

His Leu Gly Gln
20

<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1               5                   10                  15

Thr Leu Ser
```

-continued

```
<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

METHODS OF REDUCING CONCOMITANT INFECTIONS IN PIGS WITH A PCV2 ANTIGEN

RELATED APPLICATIONS

This application claims priority to U.S. patent application Ser. No. 12/198,721, which was filed Aug. 26, 2008 and issued as U.S. Pat. No. 7,829,274 on Nov. 9, 2010, and European Application Serial No. 07115609.5, filed Sep. 4, 2007, the teachings and contents of which are herein incorporated by reference.

SEQUENCE LISTING

This application contains a sequence listing in paper format and in computer readable format, the teachings and contents of which are hereby incorporated by reference. The sequence listing is identical with that incorporated in WO06/072065.

BACKGROUND OF THE INVENTION

1. Field of the Invention

The present invention relates to the field of veterinary medicine, in particular to infectious diseases. Moreover, the present invention relates to a method for reducing concomitant infections in pigs caused by pathogens other than PCV-2.

2. Description of the Related Art

In 1996 a new emerging disease termed "Postweaning Multisystemic Wasting Syndrome" (PMWS) was described in reference to cases observed in Canada five years earlier (Clark T. Pathology of the Postweaning Multisystemic Wasting Syndrome of Pigs. 1996 p. 22-5). *Porcine* cirocvirus type 2 (PCV2) was identified as an essential causative agent of this disease syndrome. PMWS has meanwhile been observed in virtually all regions of the world that produce pigs (Brunborg I M, Moldal T, Jonassen C M. J Virol Methods 2004 Dec. 15; 122(2):171-8). Pigs 5 to 15 weeks of age are most commonly affected (Allan G, McNeilly F. PMWS/PCVD: Diagnosis, Disease and Control: What do we know? 2006 Jul. 16-2006 Jul. 19; 2006; Allan G M, et al., Vet Microbiol 2004 Feb. 4; 98(2):165-8; Chae C. Vet J 2004 July; 168(1):41-9). Clinical signs include a marked increase in the mortality rate, wasting, generalized enlargment of lymphnodes, respiratory signs, and occasionally pallor, jaundice and diarrhoea (Chae C. Vet J 2005 May; 169(3):326-36; Segales J. et al. Vet Microbiol 2004 Feb. 4; 98(2):151-8). These clinical signs are not all seen at the same time in a single PMWS affected pig herd but it appears that the expression of clinical signs is indirectly linked to farm-specific co-pathogens that preferentially target different organ systems (Krakowka S. et al., Vet Pathol 2001 January; 38(1):31-42). Epidemiological investigations have shown that porcine reproductive and respiratory syndrome virus (PRRSV), swine influenza virus (SIV), porcine parvovirus (PPV), *Haemophilus parasuis, Actinobacillus pleuropneumoniae* (APP), *Streptococcus suis* and *Mycoplasma hyopneumoniae* (Chae C. Vet J 2004 July; 168(1):41-9) are most commonly seen in combination with the disease syndrome.

For the production of PMWS activation of the immune system has been postulated to be the pivotal event (Krakowka S. et al., Vet Pathol 2001 January; 38(1):31-42). While the experimental inoculation with PCV2 alone did only produce clinically asymptomatic infections and a very modest histologic evidence of inflammation the dual infection with PCV2 and PPV or PRRSV resulted in more severe clinical signs, gross and histological lesions, a wider spread and a higher PCV2 viral load within affected tissues. These findings seem to be predominantly caused by PCV2 since infection with PRRSV or PPV alone did not result in comparable clinical signs or lesions (Allan et al., J Comp Pathol 1999 July; 121(1):1-11; Allan G M, et al., Arch Virol 2000; 145(11):2421-9; Harms P A, et al., Vet Pathol 2001 September; 38(5):528-39; Krakowka S, et al., Vet Pathol 2000 May 37(3):254-63; Ostanello F, et al., Vet Microbiol 2005 Jul. 1; 108(3-4):179-86; Rovira A, et al., J Virol 2002 April; 76(7):3232-9). In addition, a similar increase in disease severity could also be achieved in the absence of other co-infecting agents if pigs were immunostimulated with keyhole limpet hemocyanin in incomplete Freund's adjuvant (KLH/ICFA) (Krakowka S. et al., Vet Pathol 2001 January; 38(1):31-42).

The effects of PCV2 on the pig immune system are not fully known. It has been reported that the main target cells for PCV2 replication are the monocyte/macrophage lineage as well as other antigen presenting cells such as follicular dendritic cells (Darwich L, et al., Arch Virol 2004 May; 149(5):857-74). Several studies suggested that PCV2 infects dividing cells, macrophages and B lymphocytes, inducing apoptosis of the B cells that leads to the damage of lymphoid tissues resulting in extensive lymphocyte depletion (Darwich L, et al., Arch Virol 2004 May; 149(5):857-74). Particularly PMWS affected pigs show histiocytic infiltration and lymphocyte depletion of both follicle centers and parafollicular zones, symptoms associated with the presence of PCV2 (Segales J. et al. Vet Microbiol 2004 Feb. 4; 98(2):151-8; Darwich L, et al., Arch Virol 2004 May; 149(5):857-74). These facts have led some to suggest that PCV2 infection might cause immunosuppression (Darwich L, et al., Arch Virol 2004 May; 149(5):857-74; Krakowka S, et al., Viral Immunol 2002; 15(4):567-82).

Approaches to treat PCV2 infections, in particular PMWS, based on a DNA vaccine are described in U.S. Pat. No. 6,703,023. In WO 03/049703 production of a live chimeric vaccine is described, comprising a PCV1 backbone in which an immunogenic gene of a pathogenic PCV2 strains replaces a gene of the PCV1 backbone. WO99/18214 has provided several PCV2 strains and procedures for the preparation of a killed PCV2 vaccine. An effective ORF-2 based subunit vaccine has been reported in WO06/072065. Any of such vaccines are intended to be used for the vaccination/treatment of swine against PMWS.

No reports exist about the potential impact of PCV2 infections on the incidence of concomitant infections caused by various swine relevant pathogens. Particularly, nothing is reported about the potential impact of PCV2 on specific pathogens, such as *Actinobacillus pleuropneumoniae, Haemophilus parasuis, Mycoplasma hyorhinis, Pasteurella multocida*, PRRSV, *Salmonella* spp., SIV or *Strepococcus suis*. Moreover, even if different PCV2 vaccines are known for a short time, their impact on concomitant infections other than PCV2 in swine is yet not known.

BRIEF DESCRIPTION OF THE DRAWINGS

FIG. 1: Profile of PCV2 viraemia. Blood samples from pre-selected placebo-treated animals (FIG. 1A; n=110) and vaccinated animals (FIG. 1B; n=110) were collected at the indicated time points. On the basis of the quantitative PCR results animals were grouped into classes of animals with sub-clinical viral loads ($10^4$-$10^6$ gE/ml) and clinical relevant viral loads (>$10^6$ gE/ml). White bars represent the proportion of animals with subclinical viral loads and black bars illustrate the proportion of animals with clinical relevant viral loads per sampling day.

DESCRIPTION OF THE INVENTION

The present invention is based on the surprising finding, that PCV2 vaccine cannot only reduce the percentage of PCV2 infections in pigs or a herd of pigs, but also the percentage of concomitant infections caused by pathogens other than circovirus, in particular other than PCV2.

Therefore, according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen.

The term "concomitant infections" as used herein shall mean but is not limited to any infection of swine caused by viral, bacterial, fungal or worm pathogens other than circovirus, in particular other than PCV2. The term "concomitant pathogen" as used herein means but is not limited to a pathogen of swine other than circovirus, in particular other than PCV2. Thus according to another aspect, the present invention provides a method for reducing the percentage of concomitant infections in pigs or a herd of pigs caused by one or more viral, bacterial, fungal or worm pathogens other than circovirus, in particular other than PCV2 comprising the step administering to said pig(s) an effective amount of PCV2 antigen or an immunogenic composition comprising PCV2 antigen. Preferably, the concomitant infections are caused by one or more bacterial, viral or fungal pathogens, or combinations thereof. More preferred, the concomitant infections are caused by one or more bacterial or viral pathogens, or a combination thereof.

According to another aspect of the present invention, the term "concomitant infections" also means that the pig infected with one or more concomitant pathogens other than circovirus, in particular other than PCV2 is co-infected with PCV2. Thus according to another aspect, the present invention provides a method for reducing the percentage of concomitant infections in pigs or a herd of pigs co-infected with PCV2, wherein the concomitant infections are caused by one or more pathogens other than circovirus, in particular other than PCV2 comprising the step administering to said pig(s) an effective amount of PCV2 antigen or an immunogenic composition comprising PCV2 antigen. Preferably, the concomitant infections are caused by one or more viral, bacterial, fungal or worm pathogens other than circovirus, in particular other than PCV2.

The term "co-infected with PCV2" as used herein means but is not limited to any form of co-infection with PCV2, which means that the PCV2 infection occurs prior to, simultaneously with or after the infection with the pathogens which are different from circovirus, in particular different from PCV2. It also includes sub-clinical, clinical apparent, fulminant and chronic courses of PCV2 infections. In this context, apparent courses are not limited to PMWS, but also include any other clinical appearances of PCV2 infections such as porcine respiratory disease complex (PRDC), porcine dermatopathy and nephropathy syndrome (PDNS), reproductive failure, granulomatous enteritis, potentially, congenital tremors (CT-AII) and perinatal myocarditis (Chae, Veterinary J., 2005; 169: 326-336).

However, the term "concomitant infection" does not necessarily mean that the pig or herd of pigs is co-infected with PCV2. The term "concomitant infection" also refers but is no limited to cases, where pigs or a herd of pigs are/is exposed to PCV2 or where a risk exist to get infected with PCV2. Thus according to another aspect, the present invention provides a method for reducing the percentage of concomitant infections in pigs or a herd of pigs exposed to PCV2, or endangered or susceptible to get infected with PCV2, wherein the concomitant infections are caused by one or more pathogens other than circovirus, in particular other than PCV2 comprising the step administering to said pig(s) an effective amount of PCV2 antigen or an immunogenic composition comprising PCV2. Preferably, the concomitant infections are caused by one or more viral, bacterial, fungal or worm pathogens other than circovirus, in particular other than PCV2.

The term "the percentage of concomitant infections is reduced" shall mean that the number of pigs infected with a pathogen other than circovirus, is reduced for said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. In this context the term "non-vaccinated control group" shall mean a group of pigs which are not administered with an effective amount of PCV2 antigen or an immunogenic composition comprising PCV2 antigen. Thus, according to another aspect, the present invention also provides a method for reducing the percentage of concomitant infections in pigs or a herd of pigs caused by a pathogen other than PCV2 comprising the step administering to said pig(s) an effective amount of PCV2 antigen or an immunogenic composition comprising PCV2 antigen, wherein the number of pigs infected with said pathogen other than circovirus, is reduced for said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Preferably, the concomitant infection is caused a by viral, bacterial or fungal pathogen other than circovirus, in particular other than PCV2. More preferably, said pigs or herd of pigs are co-infected with PCV2 as defined above, exposed to PCV2, or endangered or susceptible to get infected with PCV2.

Concomitant infections caused by a viral, bacterial or fungal pathogen other than circovirus, in particular other than PCV2 may cause enteric, respiratory, reproductive, central nervous or locomotory symptoms in the infected animals. Incidence of any of those clinical symptoms, caused the by the respective pathogens can be reduced. Thus according to another aspect, the present invention relates to a method for reducing the percentage of concomitant infections in pigs or a herd of pigs caused by one or more enteric, respiratory, reproductive, central nervous or locomotory pathogens other than PCV2 comprising the step administering to said pig(s) an effective amount of PCV2 antigen or an immunogenic composition comprising PCV2 antigen. Preferably, said pigs are co-infected with PCV2 as defined above, exposed to PCV2, or endangered or susceptible to get infected with PCV2. More preferred, the number of pigs infected with an enteric, respiratory, reproductive, central nervous or locomotory pathogen other than circovirus, is reduced for said enteric, respiratory, reproductive, central nervous or locomotory pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

Enteric pathogens are for example *Lawsonia intracellularis, E. coli, Streptococcus suis, Clostridium* spp, *Salmonella* spp., *Brachyspira* spp., rotaviruses or coronaviruses. Respiratory pathogens are for example PRRSV, *Mycoplasma hyopneumoniae, M. hyorhinis*. Reproductive pathogens are for example *Leptospira* spp., PRRSV, *Chlamydia* spp. Locomotory pathogens are for example *S. suis, M. hyorhinis, Erysipelotrix rusiopathiae*. Pathogens of the central nervous system are for example Pseudorabies virus, *S. suis., Haemophilus* sp.

In general the term "pathogen other than PCV2" means but is not limited to one or more of the pathogens selected from the group consisting of: *Actinobacillus suis; Arcanobacterium pyogenes; Actinobacillus pleuropneumonia* (APP); African swine fever virus; *Aspergillus* spp.; Astroviruses; *Ascaris suum; Blastocystis* spp.; *Bordetella bronchiseptica; Brachyspira* spp., *B. hyodysenteriae, B. pilosicoli; Brucella suis, Brucella suis* biovars 1, 2 and 3; *Candida* spp.; Classical swine fever virus; *Clostridium* spp., in particular *C. difficile, C. perfringens* types A, B and C, *C. novyi, C. septicum, C. difficile, C. tetani; Chlamydia* spp., *Cryptosporidium* spp.; Encephalomyocarditis virus; *Eperythrozoonosis suis; Erysipelothrix ruhsiopathiae; Escherichia coli; Fusarium* spp.; *Haemophilus parasuis*; Hemagglutinating encephalomyelitis virus; Hepatitis E virus; Japanese encephalitis virus; *Hyostrongylus rubidus; Lawsonia intracellularis; Leptospira* spp., *L. australis, L. canicola, L. grippotyphosa, L. pomona, L. icterohaemorrhagicae, L. interrogans, L. tarassovi, L. hardjo, L. sejroe, L. bratislava; Mannheimia haemolytica; Menangle virus; Mycobacterium* spp., *M. avium, M. intracellulare, M. tuberculosis; Mycoplasma* spp., *M. hyopneumoniae, M. hyorhinis; Nipah virus; Oesophagostum* spp., *Oesophagostum dentatum, Oesophagostum quadrospinulatum; Pasteurella* spp., *P. multocida; Penicillium* spp.; *Porcine* adenovirus; *Porcine* cytomegalovirus; *Porcine* enteric caliciviruses; *Porcine* enteric picornaviruses; *Porcine parvovirus; Porcine* respiratory corona virus; PRRS virus; Pseudorabies virus; Reovirus; Rotavirus; *Rubulavirus; Salmonella* spp., *S. typhimurium, S. choleraesuis, S. dublin; Sarcoptes* spp.; *Staphylococcus hyicus; Streptococcus* spp., *S. suis, S. porcinus, S. dysgalactiae, S. dysgalactiae* subsp. *equisimilis; Strongyloides ransomi*; Swine herpes virus; Swine influenza virus; Swine pox virus; Transmissible gastroenteritis virus; *Trichuris* spp. *Taenia* spp., *Trichinella spiralis*; Vesicular stomatitis virus; Virus of vesicular exanthema of swine; West Nile virus; or *Yersina* spp., *Y. pseudotuberculosis, Y. enterocolitica*.

Thus according to another aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the pathogens cause the concomitant infections are selected from the group consisting of: *Actinobacillus suis; Arcanobacterium pyogenes; Actinobacillus pleuropneumonia* (APP); African swine fever virus; *Aspergillus* spp.; Astroviruses; *Ascaris suum; Blastocystis* spp.; *Bordetella bronchiseptica; Brachyspira* spp., *B. hyodysenteriae, B. pilosicoli; Brucella suis, Brucella suis* biovars 1, 2 and 3; *Candida* spp.; Classical swine fever virus; *Clostridium* spp., in particular *C. difficile, C. perfringens* types A, B and C, *C. novyi, C. septicum, C. difficile, C. tetani; Chlamydia* spp.; *Cryptosporidium* spp.; Encephalomyocarditis virus; *Eperythrozoonosis suis; Erysipelothrix ruhsiopathiae;*

*Escherichia coli; Fusarium* spp.; *Haemophilus parasuis*; Hemagglutinating encephalomyelitis virus; Hepatitis E virus; Japanese encephalitis virus; *Hyostrongylus rubidus; Lawsonia intracellularis; Leptospira* spp., *L. australis, L. canicola, L. grippotyphosa, L. pomona, L. icterohaemorrhagicae, L. interrogans, L. tarassovi, L. hardjo, L. sejroe, L. bratislava; Mannheimia haemolytica; Menangle virus; Mycobacterium* spp., *M. avium, M. intracellulare, M. tuberculosis; Mycoplasma* spp., *M. hyopneumoniae, M. hyorhinis; Nipah virus; Oesophagostum* spp., *Oesophagostum dentatum, Oesophagostum quadrospinulatum; Pasteurella* spp., *P. multocida; Penicillium* spp.; *Porcine* adenovirus; *Porcine* cytomegalovirus; *Porcine* enteric caliciviruses; *Porcine* enteric picornaviruses; *Porcine parvovirus; Porcine* respiratory corona virus; PRRS virus; Pseudorabies virus; Reovirus; Rotavirus; *Rubulavirus; Salmonella* spp., *S. typhimurium, S. choleraesuis, S. dublin; Sarcoptes* spp.; *Staphylococcus hyicus; Streptococcus* spp., *S. suis, S. porcinus, S. dysgalactiae, S. dysgalactiae* subsp. *equisimilis; Strongyloides ransomi*; Swine herpes virus; Swine influenza virus; Swine pox virus; Transmissible gastroenteritis virus; *Trichuris* spp. *Taenia* spp., *Trichinella spiralis*; Vesicular stomatitis virus; Virus of vesicular exanthema of swine; West Nile virus; or *Yersina* spp., *Y. pseudotuberculosis, Y. enterocolitica*.

Preferably said concomitant infections are caused by one or more of the pathogens selected from the group consisting of: *Actinobacillus pleuropneumoniae; Haemophilus parasuis; Mycoplasma hyrhinis; Pasteurella multocida*; PRRS; *Salmonella* spp. and *Strepococcus suis*. Most preferred said concomitant infections are caused by one or more of the pathogens selected from the group consisting of: *Actinobacillus pleuropneumoniae; Haemophilus parasuis; Mycoplasma hyrhinis; Pasteurella multocida*; PRRS; *Salmonella* spp., and *Strepococcus suis*. More preferred said concomitant infections are caused by one or more of the pathogens selected from the group consisting of: *Actinobacillus pleuropneumoniae; Mycoplasma hyrhinis*, and PRRS. Most preferred by *Mycoplasma hyrhinis* and/or PRRS.

Preferably, said pigs are co-infected with PCV2 as defined above, exposed to PCV2, or endangered or susceptible to get infected with PCV2. More preferred, the number of pigs infected with one or more of said pathogens above other than circovirus, is reduced for said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. In case of multiple infections, the reduction rates as described above refer to each specific pathogen. For example, reduction of more than 10% concomitant infections in a multiple infected pig means that the infection rate with regard to a specific pathogen is reduced for more than 10%. It does not necessarily mean that the infection rate with regard to all pathogen is reduced for more than 10% as compared to a non-vaccinated control group, or with regard to a herd of pigs that less than 10% of the pigs of said herd are infected by all of said pathogens.

The terms "PCV2 antigen" as used herein refer to an amino acid sequence which elicits an immune response against PCV2 in a host. An antigen, as used herein, includes the full-length sequence of any PCV2 proteins, analogs thereof, or immunogenic fragments thereof.

The term "immunogenic fragment" refers to a fragment of a protein which includes one or more epitopes and thus elicits the immune response in a host. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

An "immune response" means but is not limited to the development in a host of a cellular and/or antibody-mediated immune response to an antigen, a immunogenic composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with PCV2 infections, in delay of onset of viremia, in a reduced viral persistence, in a reduction of the overall viral load and/or a reduction of viral excretion.

The terms "immunogenic composition" or "vaccine" (both terms are used synonymously) as used herein refers to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the immunogenic composition comprising PCV2 antigen a is subunit immunogenic composition, a compositions containing whole killed, or attenuated and/or inactivated PCV2. Preferably, said pigs are co-infected with PCV2 as defined above, exposed to PCV2, or endangered or susceptible to get infected with PCV2. More preferred, the number of pigs infected with said pathogens other than circovirus, is reduced with regard to one or more of said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated from. A preferred immunogenic subunit composition comprises the PCV2 ORF-2 protein as described below. Most preferred are immunogenic subunit compositions, which comprise any of the PCV2 antigens provided in WO06/072065, which are all incorporated herein by reference in their entirety.

According to further aspect, the immunogenic composition as used herein most preferably comprises the polypeptide, or a fragment thereof, expressed by ORF-2 of PCV2. PCV2 ORF-2 DNA and protein, used herein for the preparation of the compositions and within the processes provided herein is a highly conserved domain within PCV2 isolates and thereby, any PCV2 ORF-2 would be effective as the source of the PCV2 ORF-2 DNA and/or polypeptide as used herein. A preferred PCV2 ORF-2 protein is that of SEQ ID NO: 11 of WO06/072065. A further preferred PCV ORF-2 polypeptide is provided as SEQ ID NO: 5 of WO006/072065. However, it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% of the protective immunity as compared to the PCV2 ORF-2 protein, encoded by the polynucleotide sequence of SEQ ID NO:3 or SEQ ID NO:4 as provided in WO06/072065.

Thus according to one aspect, the present invention relates to a method for reducing the percentage of concomitant infections in pigs or a herd of pigs caused by pathogens other than PCV2 comprising the step administering to said pig(s) an effective amount of PCV2 antigen or an immunogenic composition comprising PCV2 antigen, wherein the PCV2 antigen is an antigen PCV2 ORF-2 protein that has at least 70%, preferably, 80% even more preferably 90% of the protective immunity as compared to compared to the PCV2 ORF-2 protein, encoded by the polynucleotide sequence of SEQ ID NO:3 or SEQ ID NO:4 as provided in WO06/072065. Preferably said PCV2 ORF-2 have the sequence of SEQ ID NO: 11 or SEQ ID NO: 5 of WO06/072065. Preferably, said pigs are co-infected with PCV2 as defined above, exposed to PCV2, or endangered or susceptible to get infected with PCV2. More preferred, the number of pigs infected with said pathogens other than circovirus, is reduced for more than 40%, preferable for more than 50%, more preferred for more than 60%, even more preferred for more than 80% even more preferred for more than 100% as compared to a non-vaccinated control group.

In some forms, immunogenic portions of PCV2 ORF-2 protein are used as the antigenic component in the immunogenic composition, comprising PCV2 antigen. The term "immunogenic portion" as used herein refers to truncated and/or substituted forms, or fragments of PCV2 ORF-2 protein and/or polynucleotide, respectively. Preferably, such truncated and/or substituted forms, or fragments will comprise at least 6 contiguous amino acids from the full-length ORF-2 polypeptide. More preferably, the truncated or substituted forms, or fragments will have at least 10, more preferably at least 15, and still more preferably at least 19 contiguous amino acids from the full-length PCV ORF-2 polypeptide. Two preferred sequences in this respect are provided as SEQ ID NO: 9 and SEQ ID NO:10 of WO06/072065. It is further understood that such sequences may be a part of larger fragments or truncated forms.

As mentioned above, a further preferred PCV2 ORF-2 polypeptide is any one encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of this PVC2 ORF-2 polypeptide is used as the antigenic component in the composition. Preferably, such truncated or substituted forms, or fragments will comprise at least 18 contiguous nucleotides from the full-length PCV2 ORF-2 nucleotide sequence, e.g. of SEQ ID NO: 3 or SEQ ID NO: 4. More preferably, the truncated or substituted forms, or fragments, will have at least 30, more preferably at least 45, and still more preferably at least 57 contiguous nucleotides of the full-length PCV2 ORF-2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, M D 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein said PCV2 ORF-2 protein is anyone of those, described above. Preferably, said PCV2 ORF-2 protein is i) a polypeptide comprising the sequence of SEQ ID NO: 5, SEQ ID NO: 6, SEQ ID NO: 9, SEQ ID NO: 10 or SEQ ID NO: 11 of WO06/07065;
ii) any polypeptide that is at least 80% homologous to the polypeptide of i);
iii) any immunogenic portion of the polypeptides of i) and/or ii);
iv) the immunogenic portion of iii), comprising at least 10 contiguous amino acids included in the sequences of SEQ ID NO: 5, SEQ ID NO: 6, SEQ ID NO: 9, SEQ ID NO: 10 or SEQ ID NO: 11 of WO06/072065;
v) a polypeptide that is encoded by a DNA comprising the sequence of SEQ ID NO: 3 or SEQ ID NO: 4 of WO006/072065;
vi) any polypeptide that is encoded by a polynucleotide that is at least 80% homologous to the polynucleotide of v);
vii) any immunogenic portion of the polypeptides encoded by the polynucleotide of v) and/or vi);
viii) the immunogenic portion of vii), wherein polynucleotide coding for said immunogenic portion comprises at least 30 contiguous nucleotides included in the sequences of SEQ ID NO: 3, or SEQ ID NO: 4 of WO06/072065.

Preferably any of those immunogenic portions have the immunogenic characteristics of PCV2 ORF-2 protein that is encoded by the sequence of SEQ ID NO: 3 or SEQ ID NO: 4 of WO06/07065.

Preferably, said infected pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

According to a further aspect, PCV2 ORF-2 protein is provided in the immunogenic composition at an antigen inclusion level effective for the treatment of animals subclinically infected with PCV2. Preferably, the PCV2 ORF-2 protein inclusion level is at least 0.2 µg antigen/ml of the final immunogenic composition (µg/ml), more preferably from about 0.2 to about 400 µg/ml, still more preferably from about 0.3 to about 200 µg/ml, even more preferably from about 0.35 to about 100 µg/ml, still more preferably from about 0.4 to about 50 µg/ml, still more preferably from about 0.45 to about 30 µg/ml, still more preferably from about 0.6 to about 15 µg/ml, even more preferably from about 0.75 to about 8 µg/ml, even more preferably from about 1.0 to about 6 µg/ml, still more preferably from about 1.3 to about 3.0 µg/ml, even more preferably from about 1.4 to about 2.5 µg/ml, even more preferably from about 1.5 to about 2.0 µg/ml, and most preferably about 1.6 µg/ml.

According to a further aspect, the PCV ORF-2 antigen inclusion level is at least 0.2 µg/PCV2 ORF-2 protein as described above per dose of the final antigenic composition (µg/dose), more preferably from about 0.2 to about 400 µg/dose, still more preferably from about 0.3 to about 200 µg/dose, even more preferably from about 0.35 to about 100 µg/dose, still more preferably from about 0.4 to about 50 µg/dose, still more preferably from about 0.45 to about 30 µg/dose, still more preferably from about 0.6 to about 15 µg/dose, even more preferably from about 0.75 to about 8 µg/dose, even more preferably from about 1.0 to about 6 µg/dose, still more preferably from about 1.3 to about 3.0 µg/dose, even more preferably from about 1.4 to about 2.5 µg/dose, even more preferably from about 1.5 to about 2.0 µg/dose, and most preferably about 1.6 µg/dose.

The PCV2 ORF-2 polypeptide used in the immunogenic composition in accordance with the present invention can be derived in any fashion including isolation and purification of PCV2 ORF2, standard protein synthesis, and recombinant methodology. Preferred methods for obtaining PCV2 ORF-2 polypeptide are provided in WO06/072065, the teachings and content of which are hereby incorporated by reference in its entirety. Briefly, susceptible cells are infected with a recombinant viral vector containing PCV2 ORF-2 DNA coding sequences, PCV2 ORF-2 polypeptide is expressed by the recombinant virus, and the expressed PCV2 ORF-2 polypeptide is recovered from the supernatant by filtration and inactivated by any conventional method, preferably using binary ethylenimine, which is then neutralized to stop the inactivation process.

The immunogenic composition as used herein also refers to a composition that comprises i) any of the PCV2 ORF-2 protein described above, preferably in concentrations described above, and ii) at least a portion of the viral vector expressing said PCV2 ORF-2 protein, preferably of a recombinant baculovirus. Moreover, the immunogenic composition can comprise i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture supernatant.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the PCV2 antigen is recombinant PCV2 ORF-2, preferably a baculovirus expressed PCV2 ORF-2. Preferably those recombinant or baculovirus expressed PCV2 ORF-2 having the sequence as described above.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture; wherein about 90% of the components have a size smaller than 1 μm.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) and inactivating agent to inactivate the recombinant viral vector preferably BEI, wherein about 90% of the components i) to iii) have a size smaller than 1 μm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) a neutralization agent to stop the inactivation mediated by the inactivating agent, wherein about 90% of the components i) to iii) have a size smaller than 1 μm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV2 ORF-2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminium hydroxide and aluminium phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 μg to about 5 mg per dose, even more preferred in an amount of about 750 μg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV2 ORF-2 protein recovered from the supernatant of in vitro cultured cells, wherein said cells were infected with a recombinant viral vector containing PCV2 ORF-2 DNA and expressing PCV2 ORF-2 protein, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

According to a further embodiment, the present invention also relates to the use of PCV2 antigen for the preparation of a immunogenic composition for the reduction of concomitant infections caused by one or more pathogens other than PCV-2 in pigs or a herd of pigs, wherein said immunogenic composition comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 µm. Preferably, said pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 µg of PCV2 ORF-2 protein described above, ii) at least a portion of baculovirus expressing said PCV2 ORF-2 protein iii) a portion of the cell culture, iv) about 2 to 8 mM BEI, v) sodium thiosulfate in equivalent amounts to BEI; and vi) about 1 mg Carbopol 971, and vii) phosphate salt in a physiologically acceptable concentration; wherein about 90% of the components i) to iii) have a size smaller than 1 µm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. Thus, the immunogenic composition as used herein also refers to a composition that comprises from about 1 ug/ml to about 60 µg/ml of antibiotics, and more preferably less than about 30 µg/ml of antibiotics.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 µm.

The immunogenic composition as used herein also refers to Ingelvac® CircoFLEX™, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA). Thus according to another aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein said immunogenic composition comprising a PCV2 antigen is Ingelvac® CircoFLEX™, CircoVac®, CircoVent and/or Suvaxyn PCV-2 One Dose®, preferably it is Ingelvac® CircoFLEX™. Preferably, said infected pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

The term "an effective amount of PCV2 antigen" as used herein means but is not limited to an amount of PCV2 antigen, that elicits or is able to elicit an immune response in an animal, to which said effective amount of PCV2 antigen is administered.

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ TCID$_{50}$ per dose, preferably about $10^{3.0}$ to about $10^{8.0}$ TCID$_{50}$ per dose, more preferably, about $10^{4.0}$ to about $10^{8.0}$ TCID$_{50}$ per dose. In particular, when modified live PCV2 is used in the vaccines, the recommended dose to be administered to the susceptible animal is preferably about $10^{3.0}$ TCID$_{50}$ (tissue culture infective dose 50% end point)/dose to about $10^{6.0}$ TCID$_{50}$/dose and more preferably about $10^{4.0}$ TCID$_{50}$/dose to about $10^{5.0}$ TCID$_{50}$/dose. In general, the quantity of antigen will be between 0.2 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified antigen is used.

Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.6 to about 16 µg/dose, even more preferably with about 0.75 to about 8 µg/dose, even more preferably with about 1.0 to about 6 µg/dose, still more preferably with about 1.3 to about 3.0 µg/dose.

The administration of PCV2 antigen to pigs does not only result in the reduction the percentage of concomitant infections caused by pathogens other than circovirus, in particular other than PCV2, but also to a general improvement of health, particularly to the resistance against such concomitant infections. Thus, according to another aspect, the present invention also relates to a method for improving the resistance of pigs against one or more concomitant infections with pathogens other than PCV2, comprising the step administering to said pig(s) an effective amount of PCV2 antigen or an immunogenic composition comprising PCV2 antigen. Preferably, said pigs are co-infected with PCV2 as defined above, exposed to PCV2, or endangered or susceptible to get infected with PCV2.

The term "improving the resistance of pigs against concomitant infections" as used herein refers but is not limited to a process wherein the number of pigs infected with a pathogen other than circovirus, is reduced with regard to said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Thus, according to another aspect, the present invention also relates to a method for improving the resistance of pigs against concomitant infections with one or more pathogens other than PCV2, comprising the step administering to said pig(s) an effective amount of PCV2 antigen or an immunogenic composition comprising PCV2 antigen, wherein the number of pigs infected with one or more of said pathogens other than circovirus, is reduced with regard to one or more of said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Preferably, said pigs are co-infected with PCV2 as defined above, exposed to PCV2, or endangered or susceptible to get infected with PCV2.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

Example 1

Detection of Concomitant Infections in PCV-2 Infected Animals

Study Population

The study was conducted in the Southern part of Germany. Hybrid pigs of commercial cross breeds (Landrace or Edelschwein (f)×Pietrain (m)) were obtained from 15 different breeding farms being part of a "pig-producer community". The breeding farms differed in size (50 to 300 sows), management and health status. Routine preventive measures of the piglets on all breeding farms included iron injection, tooth and tail cutting and castration. Following weaning at the age of approximately 4 weeks piglets of the different breeding farms were transferred to a nursery farm with an all-in-all-out production system. They were housed commingled in three barns with pens designed to hold 60 to 120 pigs per pen. Routine preventive measures at the nursery site included prophylactic treatment with tetracyclinhydrochlorid for the first ten days after arrival. Four changes of food composition were performed during nursery. The feed provided to the animals was self-prepared based on barely and minderals. At the age of approximately 12 weeks pigs were transferred to a fattening farm with an all-in-all-out production system. They were newly commingled and housed in two stables with pens designed to hold 10 to 30 pigs per pen. Three changes of food composition were performed during fattening. The feed provided was self-prepared based on barely, wheat, corn, and whey concentrate. Pigs remained at the fattening farm for 13 to 18 weeks.

Disease History

The disease pattern of PMWS had become clinically apparent approximately three years prior to study initiation in November 2002 and was serologically confirmed in December 2002. At the end of nursery/beginning of fattening animals started to show typical signs of PMWS such as wasting, respiratory signs and a marked increase in the mortality rate. The disease was complicated by co-infections with PRRSV. Mortality rate during nursery (4-12 weeks of age) usually ranged between 3.5 and 4.8% but peak levels of up to 10% mortality were also occasionally reported. During the middle to late phase of fattening respiratory signs and growth retardation were predominating in PCV2 infected animals. Mortality rate during fattening (12-26 week old pigs) was approximately 1.7-2.4% and the number of culls was 1%. Average daily weight gain was only moderate (719-731 g/day). Three months before study initiation, the diagnosis of PMWS was verified on the basis of clinical signs and PCV2 viraemia that both occurred when animals were approximately 9 to 13 weeks old. PRRSV and *Mycoplasma hyorhinis* were identified in lung lavage samples of PCV2 infected animals as coinfecting pathogens.

Test Articles

For active vaccination against PCV2, an inactivated sub-unit vaccine (Ingelvac® CircoFLEX™, Boehringer Ingelheim Vetmedica GmbH) was administered. The vaccine contained the ORF2 capsid protein of PCV2 as active component and carbomer as adjuvant. The ORF2 sequence was derived from a North American PCV2 isolate that was isolated from tonsil and liver samples of two pigs with signs of PMWS. The ORF2 sequence was subsequently inserted into a baculovirus expression system using an insect cell line derived from ovaries of the armyworm Sodoptera frugiperda (SF+ cells) as host.

As control article served a placebo containing PCV2 capsid protein-free cell culture supernatant and carbomer as adjuvant.

Experimental Design

The field trial was performed according to the principles of "Good Clinical Practice" (GCP) and followed a randomized, negative-controlled, double-blinded, parallel study design. A total of 1519 healthy piglets were equally distributed among two treatment groups with regard to initial body weight and litter assignment. One week before weaning, one group of piglets (n=754) was vaccinated with Ingelvac® CircoFLEX™ and the other group (n=765) received a placebo. The test articles were administered as a single 1 ml dose intramuscularly in the right neck region when piglets were 25.4±3.18 days (mean±S.D.) old. After weaning pigs of both treatment groups were kept in mixed groups until the end of finishing in order to maximise the uniform exposure to pathogens.

Polymerase Chain Reactions

Polymerase chain reaction assays were used as described in order to detect specific nucleic acids for PRRSV (Mardassi H, et al., J Clin Microbiol 1994; 32(9):2197-203), *Mycoplasma hyorhinis* (Caron J., et al., J Clin Microbiol 2000; 38(4):1390-6), *Mycoplasma hyopneumoniae* (Calsamiglia M, et al., J Vet Diagn Invest 1999 May; 11(3):246-51), *Streptococcus suis* (Wisselink H J, et al., J Clin Microbiol 2002 August; 40(8):2922-9), *Pasteurella multocida* (Townsend K M, et al., J Clin Microbiol 1998 April; 36(4):1096-100), *Actinobacillus pleuropneumoniae* (Schaller A, et al., Apx toxins in Pasteurellaceae species from animals. Vet Microbiol 2000 Jun. 12; 74(4):365-76), *Bordetella bronchispectica* (Hozbor D, et al., Res Microbiol 1999 June; 150(5):333-41) and *Haemophilus parasuis* (Calsamiglia M, et al., J Vet Diagn Invest 1999 March; 11(2):140-5) in lung tissue samples.

For quantification of the PCV2 viral load in serum, PCV2 genome equivalents was/is quantified according to the method described in Brunborg et al., 2004; J. Virol Methods 122: 171-178. For amplification of PCV2, primers PCV2-84-1265U21 and PCV2-84-1319L21 were/are used. The cut-off level for a positive sample was set as $10^4$ template copies per ml serum based on validation experiments. All PCV2 DNA quantification assays were performed by bioScreen GmbH, Münster, Germany.

Results

PCV2 Viraemia

It was investigated whether the onset and severity of the observed PMWS characteristic clinical signs and lesions were related to the onset of PCV2 viraemia in the blood of pre-selected "sample animals". As illustrated in FIG. 1, the onset of PCV2 viraemia started in the placebo-treated group when animals were approximately 9-10 weeks old. Peak levels with up to 85% PCV2 positive animals were reached when animals were approximately 11 to 14 weeks old. From 14 weeks of age until the end of fattening, the proportion of PCV2 viraemic animals was decreasing without however reaching baseline levels again. In the average the individual duration of viraemia lasted for 56 days (data not shown).

Compared to the placebo-treated group the proportion of PCV2 positive animals in the vaccinated group was significantly reduced (p<0.0001) with no more than 35% of positive animals at the peak of viraemia (FIG. 1B). The average duration of viraemia in vaccinated animals was reduced by 31 days (p<0.0001; data not shown).

Another focus was placed on the examination of the viral load in animals. In this study viral loads of clinical relevance ($>10^6$ gE/ml of serum) were mainly observed in placebo-treated animals in the early phase of viraemia when animals were approximately 10-15 weeks old (FIG. 1A). At the age of 11 weeks the proportion of animals with clinical relevant viral loads (40%) was higher than the proportion of animals with subclinical relevant viral loads (37%). This ratio was drastically changing at the late phase of viraemia (17-25 weeks of age) due to a significant reduction of infections with clinical relevance. In vaccinated animals that were positive for PCV2, subclinical infections were predominating at all analyzed time points (FIG. 1B).

In summary, the PCV2 profile on the selected study sites during the time of the study were characterized as follows: a) an onset of PCV2 viraemia at study week 9-10 that coincided with the onset of clinical signs and lesions of PMWS, b) a high viral load in placebo-treated animals at the early phase of PCV2 viraemia, c) a significant reduction in the duration of viraemia and in the percentage of animals with clinical and sub-clinical relevant viral loads in vaccinated animals compared to placebo-treated animals.

Presence of Concomitant Infections in Placebo-Treated Animals

The results obtained so far confirm the diagnosis of PMWS within the analyzed study population and indicate that vaccination against PCV2 can considerably protect animals from PMWS. This placebo-controlled immunization experiment therefore allowed the testing of the hypothesis that PMWS causes an underlying immunosuppression in animals. It was speculated that in the case of a PCV2 associated immundeficiency the frequency of co-infections after the onset of PCV2 viraemia would be higher in placebo-treated animals than in the vaccinated animals. In a first step the exposure of the study animals to opportunistic organisms was therefore analyzed in more detail. Since monitoring of clinical signs had shown that animals were predominately affected from respiratory signs it was decided to select lung samples of dead animals for a respective pathogen screening by PCR. In Table 3 results are presented for placebo-treated animals only, since they are considered to reflect most closely natural field conditions.

Before onset of PCV2 viraemia (3-8 weeks of age) the only pathogen that was detected in 2 out of 5 lung samples of placebo-treated animals was *Streptococcus suis*. At onset of PCV2 viraemia (9-10 weeks of age), 1 out of 8 lung samples of placebo-treated animals was found positive for PCV2 while 4 out of 8 analyzed lung samples were tested positive for PRRSV. Other pathogens detected in low numbers either alone or in combination with these two pathogens were *Mycoplasma hyorhinis*, *Mycoplasma hyopneumoniae* and *Streptococcus suis*. The highest amount of co-infecting pathogens was detected in lung samples of placebo-treated animals during the acute phase of PCV2 viraemia (11-16 weeks of age). Among the 17 lung samples tested positive for PCV2, 12 were also found to be positive for PRRSV and 13 for *Mycoplasma hyorhinis*. In addition, co-infections with *Streptococcus suis* or *Pasteurella multocida* were sporadically detected. Finally, at the late phase of viraemia (17-26 weeks of age) co-infections with *Mycoplasma hyopneumoniae* were predominating (6 out of 7 PCV2 positive lung samples) but co-infections with *Mycoplasma hyorhinis*, *Actinobacillus pleuropneumoniae* and *Streptococcus suis* were also found. For the entire time period after the onset of viraemia (9-26 weeks of life) only 2 out of 22 of lung samples of placebo-treated animals were tested positive for PCV2 alone. In most analyzed lung samples positive for PCV2 combinations of two or three opportunistic organisms were detected. During the course of the study PCV2 infection was thus seen in association with several respiratory concomitant-infections. The onset and peak of PCV2 viraemia coincided with the onsets and peaks of PRRSV and *Mycoplasma hyorhinis* co-infections whereas the late phase of PCV2 viraemia was accompanied by the onset of a *Mycoplasma hyopneumoniae* infection.

Reduction of Co-Infections by Vaccination Against PCV2

Comparison of the frequency of respiratory pathogens detected in lung samples revealed no major differences among both treatment groups for the time before onset of PCV2 viraemia (data not shown). After the onset of PCV2 viraemia (10-26 weeks of age) the proportion of lung samples of vaccinated animals which were tested positive for *Mycoplasma hyorhinis* and PRRSV was reduced by 71% (p=0.0293) and 46% (p=0.2847), respectively (Table 1).

TABLE 1

Study results of B05 BIVI 030

|  | Placebo | | Vaccine | | reduction |
|---|---|---|---|---|---|
|  | % | (N) | % | (N) | % |
| PCV2 | 92 | (24/26) | 55 | (6/11) | 40 |
| PRRSV | 50 | (13/26) | 27 | (3/11) | 46 |
| M. hyorhinis | 62 | (16/26) | 18 | (2/11) | 71 |
| M. hyopneumoniae | 23 | (6/26) | 45 | (5/11) | — |
| S. suis | 12 | (3/26) | 27 | (3/11) | — |
| P. multocida | 4 | (1/26) | 9 | (1/11) | — |
| APP | 8 | (2/26) | 0 | (0/11) | 100 |
| B. bronchiseptica | 0 | (0/26) | 0 | (0/11) | 0 |
| H. parasuis | 0 | (0/26) | 0 | (0/11) | 0 |

Furthermore lung samples from placebo-treated animals were sporadically found to be positive for *Actinobacillus pleuropneumoniae*. Slight differences in the number of lung samples positive for *Mycoplasma hyopneumoniae, Streptococcus suis* or *Pasteurella multocida* were observed in a second study among both treatment groups. As indicated in Table 2 these pathogens were either present at only low frequencies (*Streptococcus suis, Pasteurella multocida*) or did appear at the very late phase of PCV2 infection (*Mycoplasma hyopneumoniae*).

In another study (study B05 BIVI 013) a similar resistance to concomitant pathogens was observed in vaccinated animals as presented in Table 2.

TABLE 2

Study results of B05 BIVI 013

|  | Placebo | | Vaccine | | reduction |
|---|---|---|---|---|---|
|  | % | (N) | % | (N) | % |
| P. multocida | 14 | 15/109 | 0 | 0/32 | 100 |
| H. parasuis | 3 | 3/109 | 0 | 0/32 | 100 |
| Salmonella spp. | 5 | 5/109 | 0 | 0/32 | 100 |
| APP | 4 | 4/109 | 0 | 0/32 | 100 |
| S. suis | 50 | 15/30 | n.a. | n.a. | n.a. |

Under the influence of vaccination against PCV-2 the frequency of PCV2 infections as well as the frequency of *Actinobacillus pleuropneumoniae, Haemophilus parasuis, Mycoplasma hyrhinis, Pasteurella multocida*, PRRSV, *Salmonella* spp., *Strepococcus suis* co-infections was thus notably reduced.

In another study a similar resistance to *Mycoplasma hypopneumoniae* was observed in vaccinated animals also.

LITERATURE

[1] Clark T. Pathology of the Postweaning Multisystemic Wasting Syndrome of Pigs. 1996 p. 22-5.

[2] Brunborg I M, Moldal T, Jonassen C M. Quantitation of porcine circovirus type 2 isolated from serum/plasma and tissue samples of healthy pigs and pigs with postweaning multisystemic wasting syndrome using a TaqMan-based real-time PCR. J Virol Methods 2004 Dec. 15; 122(2):171-8.

[3] Allan G, McNeilly F. PMWS/PCVD: Diagnosis, Disease and Control: What do we know? 2006 Jul. 16-2006 Jul. 19; 2006.

[4] Allan G M, McNeilly F, Ellis J, et al. PMWS: experimental model and co-infections. Vet Microbiol 2004 Feb. 4; 98(2): 165-8.

[5] Chae C. Postweaning multisystemic wasting syndrome: a review of aetiology, diagnosis and pathology. Vet J 2004 July; 168(1):41-9.

[6] Chae C. A review of porcine circovirus 2-associated syndromes and diseases. Vet J 2005 May; 169(3):326-36.

[7] Segales J, Domingo M, Chianini F, et al. Immunosuppresion in postweaning multisystemic wasting syndrome affected pigs. Vet Microbiol 2004 Feb. 4; 98(2):151-8.

[8] Krakowka S, Ellis J A, McNeilly F, Ringler S, Rings D M, Allan G. Activation of the immune system is the pivotal event in the production of wasting disease in pigs infected with porcine circovirus-2 (PCV-2). Vet Pathol 2001 January; 38(1):31-42.

[9] Allan G M, Kennedy S, McNeilly F, et al. Experimental reproduction of severe wasting disease by co-infection of pigs with porcine circovirus and porcine parvovirus. J Comp Pathol 1999 July; 121(1):1-11.

[10] Allan G M, McNeilly F, Ellis J, et al. Experimental infection of colostrum deprived piglets with porcine circovirus 2 (PCV2) and porcine reproductive and respiratory syndrome virus (PRRSV) potentiates PCV2 replication. Arch Virol 2000; 145(11):2421-9.

[11] Harms P A, Sorden S D, Halbur P G, et al. Experimental reproduction of severe disease in CD/CD pigs concurrently infected with type 2 porcine circovirus and porcine reproductive and respiratory syndrome virus. Vet Pathol 2001 September; 38(5):528-39.

[12] Krakowka S, Ellis J A, Meehan B, Kennedy S, McNeilly F, Allan G. Viral wasting syndrome of swine: experimental reproduction of postweaning multisystemic wasting syndrome in gnotobiotic swine by coinfection with porcine circovirus 2 and porcine parvovirus. Vet Pathol 2000 May; 37(3):254-63.

[13] Ostanello F, Caprioli A, Di F A, et al. Experimental infection of 3-week-old conventional colostrum-fed pigs with porcine circovirus type 2 and porcine parvovirus. Vet Microbiol 2005 Jul. 1; 108(3-4):179-86.

[14] Rovira A, Balasch M, Segales J, et al. Experimental inoculation of conventional pigs with porcine reproductive and respiratory syndrome virus and porcine circovirus 2. J Virol 2002 April; 76(7):3232-9.

[15] Darwich L, Segales J, Mateu E. Pathogenesis of postweaning multisystemic wasting syndrome caused by *Porcine* circovirus 2: An immune riddle. Arch Virol 2004 May; 149(5):857-74.

[16] Krakowka S, Ellis J A, McNeilly F, et al. Immunologic features of porcine circovirus type 2 infection. Viral Immunol 2002; 15(4):567-82.

[17] Batista L. Postweaning Multisystemic Wasting Syndrom (PMWS) in Quebec, is it an emerging disease? 2006 Mar. 4-2006 Mar. 7; 2006.

[18] Blanchard P, Mahe D, Cariolet R, et al. Protection of swine against post-weaning multisystemic wasting syndrome (PMWS) by porcine circovirus type 2 (PCV2) proteins. Vaccine 2003 Nov. 7; 21(31):4565-75.

[19] Caron J., Ouardani M., Dea S. Diagnosis and differentiation of *Mycoplasma hyopneumoniae* and *Mycoplasma hyorhinis* infections in pigs by PCR amplification of the p36 and p46 genes. J Clin Microbiol 2000; 38(4):1390-6.
[20] Calsamiglia M, Pijoan C, Trigo A. Application of a nested polymerase chain reaction assay to detect *Mycoplasma hyopneumoniae* from nasal swabs. J Vet Diagn Invest 1999 May; 11(3):246-51.
[21] Wisselink H J, Joosten J J, Smith H E. Multiplex PCR assays for simultaneous detection of six major serotypes and two virulence-associated phenotypes of Streptococcus suis in tonsillar specimens from pigs. J Clin Microbiol 2002 August; 40(8):2922-9.
[22] Townsend K M, Frost A J, Lee C W, Papadimitriou J M, Dawkins H J. Development of PCR assays for species- and type-specific identification of *Pasteurella multocida* isolates. J Clin Microbiol 1998 April; 36(4):1096-100.
[23] Schaller A, Kuhnert P, de la Puente-Redondo V A, Nicolet J, Frey J. Apx toxins in Pasteurellaceae species from animals. Vet Microbiol 2000 Jun. 12; 74(4):365-76.
[24] Hozbor D, Fouque F, Guiso N. Detection of *Bordetella bronchiseptica* by the polymerase chain reaction. Res Microbiol 1999 June; 150(5):333-41.
[25] Calsamiglia M, Pijoan C, Solano G, Rapp-Gabrielson V. Development of an oligonucleotide-specific capture plate hybridization assay for detection of *Haemophilus*

---

What is claimed is:

1. A method for reducing the percentage of concomitant infections by more than 10% in pigs or a herd of pigs caused by one or more pathogens other than PCV2 comprising the step of administering to the pigs a single dose of PCV2 ORF2 composition or an immunogenic composition comprising PCV2 ORF2, wherein the PCV2 ORF2 composition or immunogenic composition comprises a polymer of acrylic or methacrylic acid and 4-400 μg PCV2 ORF2 and wherein reducing the percentage of concomitant infections occurs after a single dose and is in comparison to pigs not receiving the PCV2 ORF2 composition or immunogenic composition and wherein the concomitant infections are selected from the group consisting of *Actinobacillus pleuropneumoniae, Haemophilus parasuis, Mycoplasma hyrhinis, Mycoplasma hyopneumoniae, Pasteurella multocida, Salmonella* spp., *Strepococcus suis*, and combinations thereof.

2. The method of claim 1, wherein the pigs or herd of pigs are/is infected with PCV2.

3. A method for improving the resistance of pigs against concomitant infections with one or more pathogens other than PCV2, comprising the step of administering to the pig(s) a single dose of PCV2 ORF2 composition or an immunogenic composition comprising PCV2 ORF2, wherein the PCV2 ORF2 composition or immunogenic composition comprises a polymer of acrylic or methacrylic acid and 4-400 μg PCV2 ORF2 and wherein the number of pigs infected with one or more of the pathogens other than PCV2 is reduced with regard to one of more of the pathogens by more than 10% after a single dose of the PCV2 ORF2 composition or immunogenic composition comprising PCV2 ORF2 when compared to those pigs not receiving the PCV2 ORF2 composition or immunogenic composition, and wherein the concomitant infections are selected from the group consisting of *Actinobacillus pleuropneumoniae, Haemophilus parasuis, Myco-*

*plasma hyrhinis, Mycoplasma hyopneumoniae, Pasteurella multocida, Salmonella* spp., *Strepococcus suis*, and combinations thereof.

4. The method of claim 3, wherein the pigs are infected with PCV2.

* * * * *